United States Patent [19]

Dubois et al.

[11] Patent Number: 4,545,921

[45] Date of Patent: Oct. 8, 1985

[54] LIQUID CRYSTALS HAVING A TYPE A SMECTIC PHASE

[75] Inventors: Jean-Claude Dubois, St. Remy les Chevreuses; Gilles Ravaux, Les Ulis; Pierre Le Barny, Igny, all of France

[73] Assignee: Thomson-CSF, Paris, France

[21] Appl. No.: 566,734

[22] Filed: Dec. 29, 1983

[30] Foreign Application Priority Data

Dec. 30, 1982 [FR] France ................... 82 22074

[51] Int. Cl.$^4$ .................... C09K 3/34; C07C 121/64; C07C 69/62
[52] U.S. Cl. ................ 252/299.62; 260/465 D; 350/350 R; 350/350 S; 560/1; 560/65; 560/108; 560/139
[58] Field of Search .............. 560/108, 65, 1, 139; 252/299.62; 260/465 D

[56] References Cited

U.S. PATENT DOCUMENTS 4,112,239  9/1978  Dubois et al. ............. 560/108 X
4,402,855  9/1983  Zann et al. ............... 252/299.65

OTHER PUBLICATIONS

Demus et al., "Flussige Kristalle in Tabellen", Veb Verlag 1974, Leipzig (DD) pp. 244–245.

Primary Examiner—Dolph H. Torrence
Attorney, Agent, or Firm—Oblon, Fisher, Spivak, McClelland & Maier

[57] ABSTRACT

The invention relates to a group of organic compounds of the substituted 2-hydroxyfluorene ester type, which has a smectic A mesomorphous phase. The invention also relates to the process for producing molecules of this group.

The compound according to the invention is in accordance with the general chemical formula

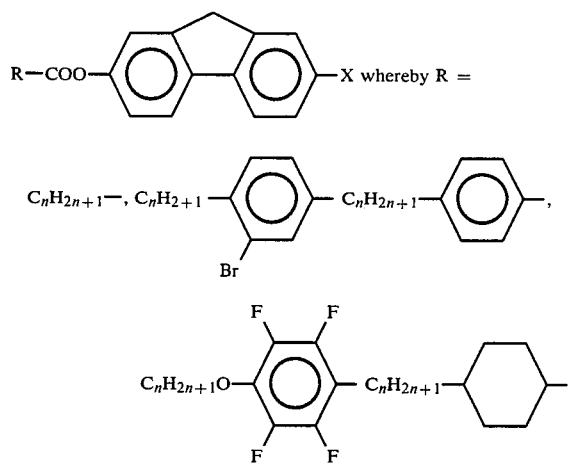

whereby n can be between 1 and 15 and X = Br or CN.

The invention applies to the field of liquid crystals and to display means using such crystals.

14 Claims, No Drawings

LIQUID CRYSTALS HAVING A TYPE A SMECTIC PHASE

BACKGROUND OF THE INVENTION

The invention relates to a group of organic compounds of the substituted 2-hydroxyfluorene ester type having a type A smectic mesomorphous phase. The invention also relates to a process for the production of the molecules of this group.

The group of compounds according to the invention is in accordance with the general chemical formula:

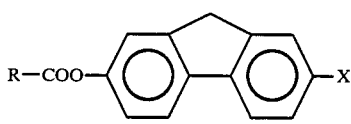

in which the radical R can be:

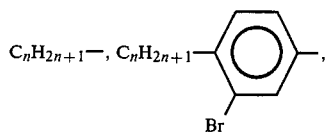

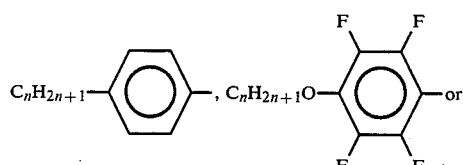

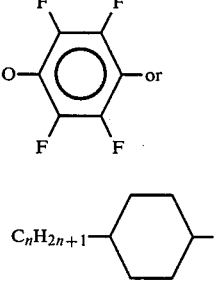

with N being 1 through 15
and X=Br or CN.

The compounds of this family can be given the following names:
2-alkanoyloxy-7-bromofluorene or cyanofluorene
2-[4'-alkyl-3'-bromobenzoyloxy]-7-bromofluorene or cyanofluorene,
2-[4'-alkylbenzoyloxy]-7-bromofluorene or cyanofluorene,
2-[4'-alkoxyfluorobenzoyloxy]-7-bromofluorene or cyanofluorene,
2-[trans-4'-alkylcyclohexane-carbonyloxy]-7-bromofluorene or cyanofluorene.

The following description relates to the general synthesis process for the molecules according to the invention, as well as to the mesomorphous properties of the corresponding liquid crystals.

GENERAL SYNTHESIS PROCESS

The organic group according to the invention has a radical R, which is obtained by chemical reactions, which differ relatively significantly from one another as a function of the individual case. For reasons of clarity in the description of the general synthesis process, initially the stage giving the end product will be described, followed by the basic products and details of the production procedure.

(1) Synthesis of the esters according to the invention:

REACTION 1

The synthesis of these esters takes place in one stage from the chloride of acid

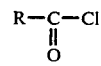

and a phenol (2-hydroxy-7-bromofluorene or cyanofluorene)

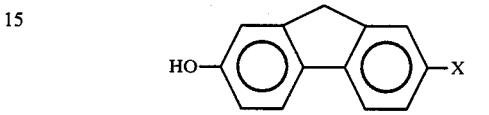

at ambient temperature, in pyridine.

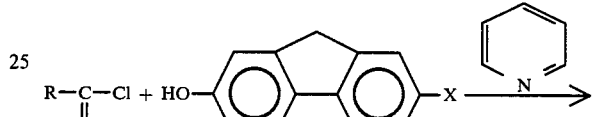

(2) Obtaining chlorides of acid

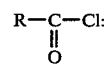

REACTION 2

The alkanoyl and 4-alkylbenzoyl chlorides are products known to the expert. The chlorides of 4-alkyl-3-bromobenzoyl, 4-alkyloxy fluorobenzoyl and 4-alkyl-cyclohexane-carbonyl are prepared in one stage from the corresponding acids by the action of thionyl chloride, in accordance with the standard reaction:

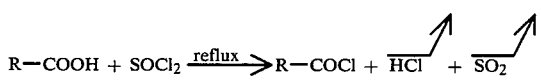

(3) Obtaining 4-alkyl-3-bromobenzoic acids:

REACTION 3

4-alkyl-3-bromobenzoic acids are prepared in one stage by a known process (cf the article by SPATH and PIHL published in the Journal BERICHTE 62, p. 2259, 1929). The bromine is reacted with an alkylbenzoic acid in the presence of silver nitrate, nitric acid and acetic acid at 25° C.

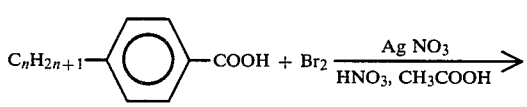

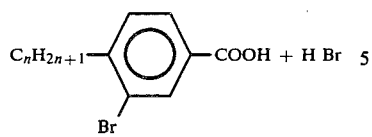

(4) Obtaining 4-alkyloxyfluorobenzoic acids:

REACTION 4

4-alkloxyfluorobenzoic acids are obtained in one stage from fluorobenzoic acid in accordance with a known operating procedure (cf BURDON, HOLLYHEAD, TATLOW, Journal of Chemistry Society, p. 6336, 1965), but modified with a view to increasing the yield. The reaction consists of reacting sodium alkoxide with a pentafluorobenzoic acid in the form of a sodium salt (sodium pentafluorobenzoate) in an alcohol used as the solvent, followed by the acidification of the reaction mixture at the end of the reaction.

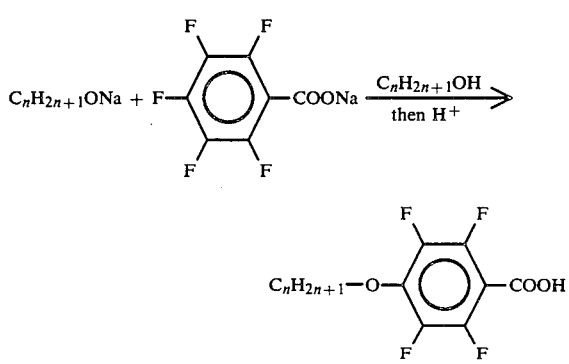

(5) Obtaining trans-alkyl-cyclohexane-carboxylic acids:

REACTION 5

These acids are prepared by the catalytic hydrogenation of alkylbenzoic acids according to the method of GRAY and McDONNELL (published in 1979 on Molecular Crystal Liquid and Crystals No. 53, pp. 147 to 166). The reaction takes place in the presence of Raney nickel W-2, at 200° C. and under a pressure of 200 bars.

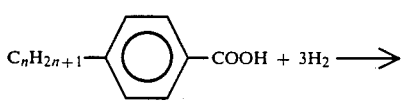

The trans-derivative is separated from the cis-derivative by an inclusion compound with thiourea.

(6) Obtaining 2-hydroxy-7-bromofluorene or cyanofluorene: 2-hydroxy-7-bromofluorene is obtained in six stages from fluorene in accordance with the following reaction diagram:

action of nitric acid on fluorene in the presence of acetic acid at 80° C.:

REACTION 6

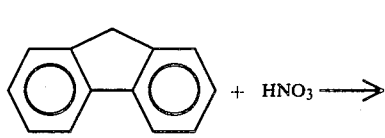

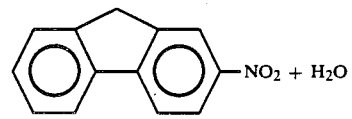

action of hydrochloric acid in the presence of iron on the organic compound obtained by reaction 6, in 90% ethyl alcohol:

REACTION 7

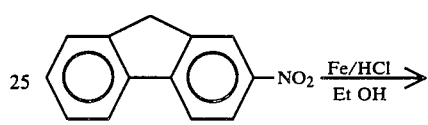

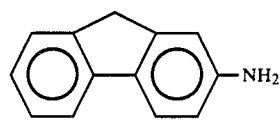

action of nitrous acid on the compound obtained in reaction 7, in the presence of pyridine. The end product is obtained by decomposition under the action of heat:

REACTION 8

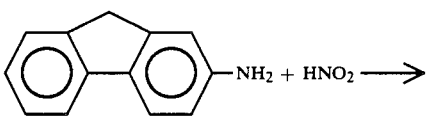

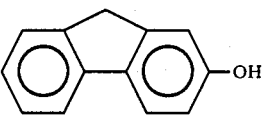

action of acetyl chloride on the product obtained in reaction 8, in the presence of toluene and pyridine:

REACTION 9

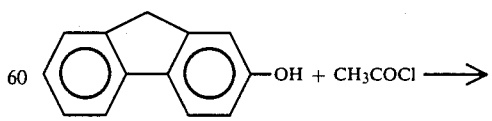

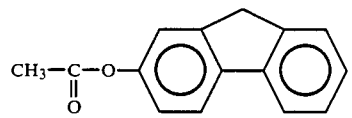

action of bromine on the compound obtained in the reaction 9 in the presence of acetic acid and acetic anhydride:

REACTION 10

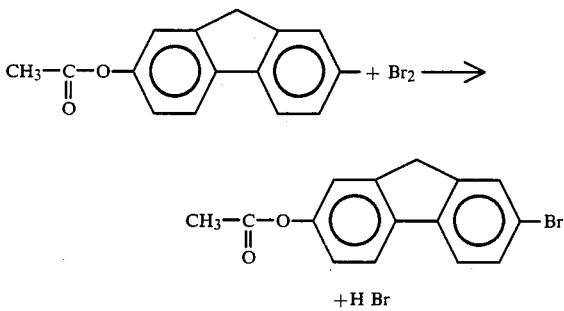

+H Br action of sodium hydroxide and then hydrochloric acid on the product obtained in reaction 10:

REACTION 11

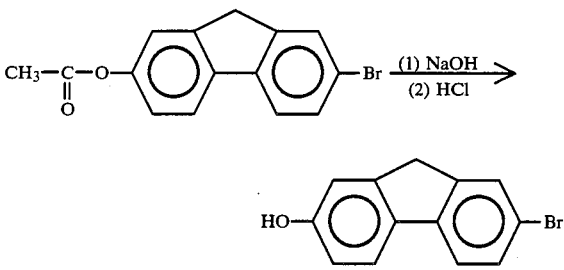

2-hydroxy-7-cyanofluorene is synthesized from 2-hydroxy-7-bromofluorene (obtained in reaction 11) by the action of cuprous cyanide in N-methyl pyrrolidone:

REACTION 12

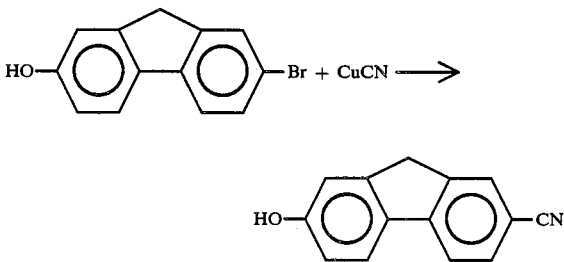

Reactions 9, 11 and 12 are of a conventional nature. Reactions 6 and 7 have been described respectively by KUHN (Organic Syntheses, Volume XII, p.74) and by GRAY, HARTLEY and IBBOTSON (Journal of Chemistry Society, p. 2687, 1955). Reaction 8 is based on the operating procedure described in "Methoden der organischem Chemie, Phenole Teil 1 K.F., Wedemeyer Georg Thieme Verlag, Stuttgart, p. 253, 1976."

OPERATING PROCEDURE FOR REACTIONS 1, 4, 8 and 10

(1) General preparation of the esters:

REACTION 1

1.5 mM of 2-hydroxy-7-bromofluorene or cyanofluorene in 3 ml of pyridine is dissolved in a 10 ml Erlenmeyer flask. The solution obtained is poured into an Erlenmeyer flask containing 1.5 mM of freshly prepared acid chloride. The reaction mixture is then stirred with a bar magnet. The reaction is continued at ambient temperature for 48 hours. The product obtained is then poured onto approximately 150 g of a water-ice mixture and the medium is slightly acidified with hydrochloric acid titrating 25%, followed by an extraction phase with methylene chloride. The organic phase is washed with water, dried on magnesium sulfate, filtered and evaporated in vacuo. The crude product is purified by liquid chromatography and exposed to the eluent toluene 50-hexane 50, followed by recrystallization in cyclohexane.

(2) Synthesis of a 4-alkyloxy fluorobenzoic acid:

REACTION 4

The reaction relates to a specific example, namely the synthesis of 4-nonyloxyfluorobenzoic acid, it being understood that the synthesis of acids of the same group can be carried out by the same method on the basis of corresponding basic constituents.

350 ml of freshly distilled 1-nonanol (in order to introduce into the future molecule according to the invention, a straight hydrocarbon chain typical of liquid crystals having a smectic phase) and then 4.6 g of purified sodium are introduced into an Erlenmeyer flask with a capacity of 1 liter and equipped with a magnetic stirrer. The mixture is heated to 60° C., accompanied by stirring until the metallic sodium disappears.

In parallel, 21.2 g of pentafluorobenzoic acid are dissolved in 200 ml of 1-nonanol, heated to 40° C. The pentafluorobenzoic acid solution is added to the sodium nonanoate solution. The reaction medium is stirred for 48 hours at a temperature of 60° C. The reaction medium is then allowed to return to ambient temperature and is poured into 800 ml of soft water. The medium is then acidified with hydrochloric acid titrating 25% to pH=2. The organic phase is extracted with ether, washed with water up to neutrality, dried on magnesium sulphate, filtered and evaporated in vacuo.

The excess nonanol is eliminated by vacuum distillation. A viscous brown liquid, crystallizing in hexane at −18° C. is recovered from the distiller. The precipitate obtained is filtered, washed with cold hexane and then recrystallized in hexane. 4.93 g of acid are obtained. The reaction yield is 14.7%. The melting point of the product obtained is F=57° C.

(3) Synthesis of 2-hydroxyfluorene:

REACTION 8

195 ml of sulphuric acid and 95 ml of water are mixed by vigorous stirring in a reactor with a capacity of 1 liter. The sulphuric acid solution obtained is then cooled to 0° C. by means of a mixture of acetone and solid carbon dioxide. 19.5 g of sodium nitrite is added in small quantities to this solution. The resulting product has a milky appearance. It is heated on the water bath at a temperature of approximately 40° to 50° C., until a clear yellow solution is obtained. The reaction medium is then cooled to 0° C. by means of a mixture of acetone and solid carbon dioxide. A solution of 23.5 g (0.13 mole) of the product obtained in the reaction of 7-

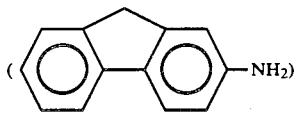

in 130 ml of pyridine is added dropwise thereto, accompanied by stirring. Stirring is continued at 0° C. for 1 hour. The content of the reactor is then transferred into a 4 liter round-bottomed flask, which has been previously cooled to −18° C. An adequate quantity of water for obtaining a total volume of 2.5 liters is then added thereto. This is followed by the addition of an aqueous solution of 13 g of urea and magnetic stirring is continued for 1 hour at a temperature of 0° C.

In parallel, 5 liters of water are boiled in a 10 liter reactor, followed by the rapid addition thereto of the reaction mixture. The total mixture is then refluxed for 1 hour. On returning to ambient temperature, the precipitate which appears is filtered.

The crude phenol obtained is dissolved in 2 liters of soda (concentration 10%) heated to boiling. An insoluble, maroon-coloured substance forms, which is filtered hot. The hot filtrate is acidified with hydrochloric acid titrating 37%, accompanied by stirring. The phenol precipitates, is filtered, washed with water and then dried in vacuo on phosphoric anhydride $P_4O_{10}$. 15 g of phenol are obtained. The reaction yield is 63.5% and the melting point of the product obtained F=167° C.

(4) Synthesis of 2-acetoxy-7-bromofluorene:

REACTION 10

20 g of 2-acetyloxyfluorene (89.3 mM) obtained as a result of the preceding reaction, 110 ml of acetic acid and 55 ml of acetic anhydride are introduced into a 500 ml Erlenmeyer flask, in which magnetic stirring takes place and which is equipped with a reflux condenser and a dropping funnel. The Erlenmeyer flask is heated to 60° C. by means of an oil bath, in order to dissolve the ester, followed by the addition of 4.9 mg of iodine. Heating is stopped and 43 g of bromine are added dropwise, whilst stirring for 30 minutes.

On return to ambient temperature, the solution is decolorized. The Erlenmeyer flask is then immersed in a bath of water and ice. A precipitate then appears, which is filtered and the insoluble part is washed with hexane and then with water. 18.17 g of white bromine derivative is obtained. Water is added to the filtrate and a precipitate appears, which is filtered, washed with water and dried. The second precipitate is purified by recrystallizing in ether and −18° C., followed by filtration on silica with benzene as the eluent. This leads to 1.56 g of 2-acetoxy-7-bromofluorene. The reaction yield is 72.9%. The melting point of the product obtained is F=128° C.

PROPERTIES OF THE SYNTHESIZED SUBSTANCES

The following tables 1 and 2 give the calorimetric study carried out on several compounds of the group of 2-bromofluorene or 2-cyanofluorene esters according to the invention. As a function of the radicals R and X allocated to the molecules, it is possible to know at what temperature the transitions take place between the different phases: from the crystalline phase (K) to the liquid phase (L), whilst passing through the smectic phase A($S_A$) and possibly the nematic phase (N). The transition temperatures are given in oC. The values in round brackets are temperatures corresponding to the monotropic phases and the values in square brackets are transition enthalpies in kcal/mole.

The nature of the mesophases was determined by the study of the isomorphism under the optical microscope of the studied compounds with known substances. All the esters appearing in the tables have a smectic A mesophase and sometimes a monotropic mesophase and in certain cases even a nematic phase.

Study of table 1 shows that the ester no. 1 (corresponding to R=$C_7H_{15}$-and X=Br) has a monotropic smectic phase A. When the temperature of this crystal rises, it passes directly from the crystalline phase into the liquid phase, the phase transition taking place at 101° C. On cooling, the crystal returns to the crystalline phase, whilst having a smectic phase for a temperature of 98.5° C. Ester no. 4 (R=$C_9H_{19}$- and X=CN) also has a monotropic smectic phase.

Certain esters such as 10, 11, 12 and 13 also have a nematic phase, as well as the smectic phase (table 2).

The calorimetric study revealed that 2-alkanoyloxy-7-bromofluorene

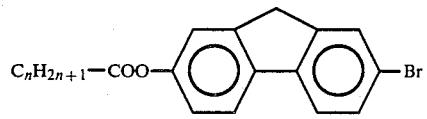

are not mesomorphous for n<7 and that 2-alkanoyloxy-7-cyanofluorenes

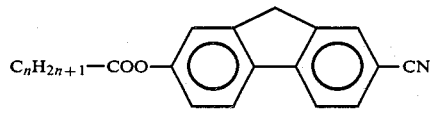

are not mesomorphous for n<9. However, the other esters according to the invention have a smectic phase for values of n between 1 and 15.

It falls within the scope of the invention to use the thus defined organic compounds as smectic liquid crystals, either alone or mixed with one another or mixed with other products, said mixture also having a smectic phase. It can be used in display means.

TABLE 1

| No | R | X | K | | $S_A$ | | L |
|----|---|---|---|---|-------|---|---|
| 1 | $C_7H_{15}$— | Br | x | | | 101 [5.49] | x |
| | | | | x | (98.5) [1.14] | | x |
| 2 | $C_8H_{17}$— | Br | x 85.3 [4.13] | x | | 92.4 [1.14] | x |
| 3 | $C_9H_{19}$— | Br | x 85 [4.80] | x | | 95 [1.3] | x |
| 4 | $C_9H_{19}$— | CN | x | | | 71.9 [8.81] | x |
| | | | | x | (69) [0.93] | | x |
| 5 | $C_{11}H_{23}$— | CN | x 81 [8.16] | x | | 84.2 [0.80] | x |
| 6 | $C_{13}H_{27}$— | CN | x 76.4 [8.07] | x | | 91.5 [0.92] | x |
| 7 | $C_{14}H_{29}$— | CN | x 80.4 [9.17] | x | | 92.9 [1.12] | x |
| 8 | $C_{10}H_{21}$—⟨O⟩— | CN | x 125.5 [6.57] | x | | 192 [0.60] | x |
| 9 | $C_7H_{15}$—⟨O⟩—Br | Br | x 107.8 [7.10] | x | | 139.3 [0.78] | x |

TABLE 2

| No | R | X | K | | $S_A$ | | N | | L |
|----|---|---|---|---|-------|---|---|---|---|
| 10 | $C_9H_{19}-\bigcirc-$ | CN | X | 96 [4.68] | X | 209 [0.17] | X | 210 [0.14] | X |
| 11 | $C_7H_{15}-\bigcirc-$ | CN | X | 140.5 [6.32] | X | 153 | X | 204.8 [0.16] | X |
| 12 | $C_8H_{17}-\bigcirc-$ | CN | X | 134.8 [6.51] | X | 182.5 [0.03] | X | 198.5 [0.12] | X |
| 13 | $C_9H_{19}O-\bigcirc-$ (F,F,F,F) | CN | X | 109 [11.54] | X | 140.5 [0.05] | X | 152.5 [0.11] | X |

What is claimed is:

1. An organic compound of the substituted fluorene ester type, having at least one smectic A mesomorphous phase, in accordance with the general formula:

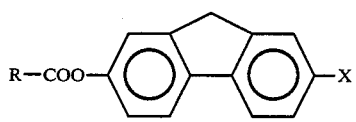

for which R is:
$C_nH_{2n+1}$-with N being 7 through 15 and X=Br
$C_nH_{2n+1}$-with N being 9 through 15 and X=CN

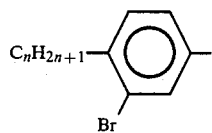

with N being 1 through 15 and X=Br or CN

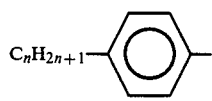

with N being 1 through 15 and X=Br or CN

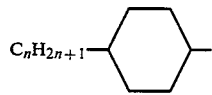

with N being 1 through 15 X=Br or CN

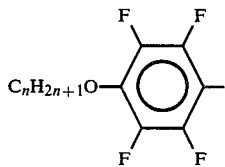

with N being 1 through 15 and X=Br or CN.

2. An organic compound according to claim 1, wherein R=$C_8H_{17}$- and X=Br.
3. An organic compound according to claim 1, wherein R=$C_9H_{19}$- and X=Br.
4. An organic compound according to claim 1, wherein R=$C_{11}H_{23}$- and X=CN.
5. An organic compound according to claim 1, wherein R=$C_{13}H_{27}$- and X=CN.
6. An organic compound according to claim 1, wherein R=$C_{14}H_{29}$- and X=CN.
7. An organic compound according to claim 1, wherein

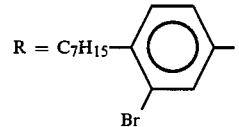

and X=Br.

8. An organic compound according to claim 1, wherein

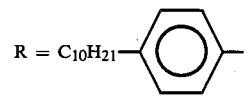

and X=CN.

9. An organic compound according to claim 1, wherein

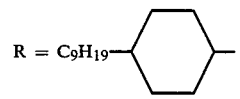

and X=CN, said compound also having a nematic phase.

10. An organic compound according to claim 1, wherein

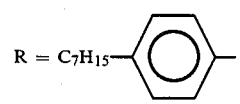

and X=CN, said compound also having a nematic phase.

11. An organic compound according to claim 1, wherein

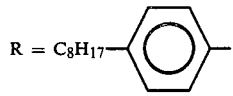

and X=CN, said compound also having a nematic phase.

12. An organic compound according to claim 1, wherein

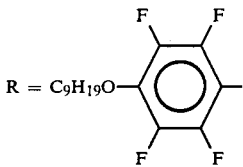

and X=CN.

13. A liquid crystal which comprises a mixture of organic compounds wherein at least one organic compound is a compound according to claim 1, said mixture having at least one smectic phase.

14. A smectic liquid crystal display in which the liquid crystal comprises a mixture of organic compounds wherein at least one organic compound is a compound according to claim 1.

* * * * *